United States Patent [19]

Jones

[11] 4,179,458
[45] * Dec. 18, 1979

[54] PROCESS FOR PREPARING ORGANOTIN COMPOUNDS

[75] Inventor: Trevor E. Jones, Halesowen, England

[73] Assignee: Albright & Wilson Limited, Warley, England

[*] Notice: The portion of the term of this patent subsequent to May 30, 1995, has been disclaimed.

[21] Appl. No.: 759,179

[22] Filed: Jan. 13, 1977

[30] Foreign Application Priority Data

Jan. 14, 1976 [GB] United Kingdom ............... 1461/76
Jul. 19, 1976 [GB] United Kingdom ............. 29937/76

[51] Int. Cl.$^2$ ............................................. C07F 7/22
[52] U.S. Cl. ................................................ 260/429.7
[58] Field of Search ................................... 260/429.7

[56] References Cited

U.S. PATENT DOCUMENTS

| | | |
|---|---|---|
| 2,679,506 | 5/1954 | Rochow ............................ 260/429.7 |
| 2,852,543 | 7/1958 | Blitzer et al. .................... 260/429.7 |
| 3,085,102 | 4/1963 | Yatagaj et al. ................... 260/429.7 |
| 3,415,857 | 12/1968 | Hoye .................................. 260/429.7 |
| 3,475,473 | 10/1969 | Tahara et al. .................... 260/429.7 |
| 3,547,965 | 12/1970 | Takubo et al. ................... 260/429.7 |
| 3,651,108 | 3/1972 | Giannaccari et al. ............ 260/429.7 |
| 3,954,820 | 5/1976 | Menon .............................. 260/429.7 |
| 4,092,340 | 5/1978 | Jones ................................ 260/429.7 |

FOREIGN PATENT DOCUMENTS 736822 9/1955 United Kingdom .................. 260/429.7

OTHER PUBLICATIONS

Luijten et al., Investigations in the Field of Organotin Chemistry, Tin Res. Inst. England, pp. 11 to 13, 25 to 33, 85 & 86 (1955).
Lietz et al., J. Org. Chem., vol. 22, pp. 60–62 (1957).
Sawyer, Organotin Compounds, Marcel-Dekker, Inc., N.Y., VI, pp. 82 to 84 (1971).

Primary Examiner—Helen M. S. Sneed
Attorney, Agent, or Firm—Frishauf, Holtz, Goodman & Woodward

[57] ABSTRACT

Organotin compounds comprising at least 50% and often at least 90% tetraorganotin compound and the remainder triorganotin halide, which are suitable for conversion to organotin precursors of stabilizers for polymers or fungicides, are made by reacting an alkyl or alkenyl halide with a mixture of tin and zinc (or alloy thereof) with an atomic ratio of at least 0.5:1 zinc to tin, in a liquid comprising an 'onium salt, to produce the organotin compound at least some of which is in the liquid.

24 Claims, No Drawings

PROCESS FOR PREPARING ORGANOTIN COMPOUNDS

This invention relates to a process for preparing tetraorganotin compounds from elemental tin.

Organotin compounds can be prepared by reaction of tin halides with organo-metallic compounds such as Grignard reagents. Processes have also been described in which organotin compounds are prepared directly from elemental tin. Thus our British Patent Specification No. 1,115,646 describes a process for preparing predominantly diorganotin dihalides which comprises reacting tin with an aliphatic halide in the presence of a nitrogen, sulphur or phosphorus 'onium compound and a preformed tin II halide or organotin halide and in the optional presence as cocatalyst of a small amount of a metal which may be zinc among many others. In U.S. Pat. No. 3,085,102 is described a similar process, but without the 'onium compound and preformed halide, but in which the cocatalyst is essential and is preferably magnesium. U.S. Pat. No. 3,547,965 describes the preparation of triorganotin halides by reaction of organic halides with an equiatomic mixture of tin and zinc in the presence of an alcohol. U.S. Pat. No. 3,651,108 describes the preparation of tetra organotin compounds by reaction of organic halides in the presence of an 'onium compound, or Lewis base, with tin and an alkaline or alkaline earth metal, in particular magnesium.

A process for preparing tetraorganotin compounds without using the hazardous alkaline or alkaline earth metals is described in our prior patent application No. 648,948 filed Jan. 14, 1976, as a process for preparing a tetraalkyltin compound which comprises passing a halide of formula RX where R is an alkyl group of 1 to 4 carbon atoms and X is a chlorine, bromine or iodine atom, into a heated suspension of metallic material, which is zinc and tin, or an alloy of tin and zinc, the atomic proportion of zinc to tin in said material being at least 0.5:1, in a liquid comprising at least one organic quaternary ammonium or phosphonium salt or tertiary sulphonium salt, to produce a vapour effluent comprising substantially all the tetraalkyltin compound prepared.

We have now found a process wherein the tetraorganotin compound may be prepared in the liquid phase, without use of the hazardous alkali metals or alkaline earth metals.

The present invention provides a process for preparing a tetra organotin compound, which comprises reacting an organic halide of formula RX, wherein R is an alkyl group of 1–20 carbon atoms, or alkenyl group of 2–20 carbon atoms, and X is a chlorine, bromine or iodine atom, with a heated suspension of metallic material which is zinc and tin, or an alloy of tin and zinc, the atomic proportion of zinc to tin in the material being at least 0.5:1, in a liquid comprising at least one 'onium salt, which is an organic quaternary ammonium or phosphonium salt or tertiary sulphonium salt, to produce the tetraorganotin compound at least some of which is in the liquid. The tetraorganotin compound is usually recovered at least from the liquid phase after cessation of the reaction.

The reaction is carried out under conditions such that the tetra organotin product of the reaction contains at least 50% by weight of tetra organotin and the remainder (if any) contains a substantial proportion of triorganotin halide. Preferably, the product contains at least 70% (molar percentage) of tetraorganotin and up to 30% of triorganotin halide and especially the product contains at least 90% and up to 10% of triorganotin halide. The composition of the organotin product depends for any particular combination of 'onium salt and organic halide on the molar proportion of the total of organic halide, which has reacted and is present in the liquid, to the 'onium salt; the lower the proportion is, the higher is the proportion of tetraorganotin to triorganotin halide. The molar proportion of organic halide to salt is usually less than 25:1, preferably less than 20:1, e.g. less than 15:1. The molar proportion chosen depends on the nature of the organic halide and the desired composition of the product.

It is believed that there is a critical proportion of halide to salt below which the organotin product contains at least 90% tetraorganotin; for octyl chloride the proportion is believed to be about 7:1, for butyl chloride it is believed to be in the 7–7.5:1 region, while for octyl iodide, it is believed to be in the 11–12:1 region. In a process in which organic halide is added progressively to the reaction, addition of more halide over the critical amount gives rise to a significant reduction in the proportion of tetraorganotin in the product and often is accompanied by a rapid production of a gaseous by-product believed to be the olefin corresponding to elimination from the organic halide.

In a preferred aspect the present invention provides a process for preparing a tetraorganotin compound, which comprises reacting an organic halide of formula RX, wherein R is an alkyl group of 1–20 carbon atoms, or alkenyl group of 2–20 carbon atoms, and X is a chlorine, bromine or iodine atom, with a heated suspension of metallic material which is zinc and tin, or an alloy of tin and zinc, the atomic proportion of zinc to tin in the material being at least 0.5:1, in a liquid comprising at least one organic quaternary ammonium or phosphonium salt or tertiary sulphonium salt, to produce a tetra organotin compound, at least some of which is in the liquid, the molar proportion of organic halide to salt being less than the critical proportion (especially up to 7:1) so that the organotin product of the reaction comprises at least 90% of the tetraorganotin and less than 10% of triorganotin halide. The tetraorganotin compound is usually recovered at least from the liquid phase after cessation of the reaction.

The organic group in the organic halide may be methyl, ethyl, n or isopropyl, n-, sec- iso- or tert-butyl, octyl, e.g. n-octyl, vinyl or allyl. The organic halide is preferably an alkyl or alkenyl halide each of 2 to 8, especially 4 to 8 carbon atoms. Butyl chloride and octyl chlorides are preferred. A mixture of organic halides may be used to give a mixture of tetraorganotin products. The amount of organic halide added is usually at least two moles per g atom of tin, e.g. 2.5–15 and preferably 2.5–7, e.g. 2.5–5 moles per g atom of tin; the total amount of organic halide added depends on the degree to which the reaction is taken to completion, i.e. for 100% reaction at least four moles organic halide per g atom of tin or 2 moles per g atom of zinc (whichever is the smaller) is needed. The amount of halide added also depends on the amount which is unreacted and boils off as a gaseous effluent. When the process is for preparing organotin compounds comprising at least 90% tetraorganotin, the molar proportion of organic halide to salt is usually up to the critical proportion, e.g. from 4:1 to that proportion, such as up to 7:1, preferably 4 to 6.8:1, e.g. 5–6.7:1, especially 6–6.7:1. Especially preferred as a molar proportion is one in the range of x-1:1 to x:1 where x is the critical proportion.

The liquid contains the organic quaternary ammonium, or phosphonium salt or tertiary sulphonium salt often at a temperature of 100°–300° C., e.g. 150°–250° C. preferably 150°–220° C. The salt is usually a halide, e.g. a chloride or bromide but especially an iodide; indeed, if the halide reactant is not itself an iodide, the presence of an iodide in the liquid is very desirable as it enhances the reaction rate. The salt is commonly a salt of formula $R'_4N^+Y^-$, $R'_4P^+Y^-$ or $R'_3S^+Y^-$, wherein each R' is an alkyl group, e.g. of 1–13, especially 1–8, carbon atoms, or an aralkyl group of 7–19 carbon atoms, e.g. an aralkyl hydrocarbyl group of 7–19 carbon atoms, such as benzyl, or a cycloalkyl group of 5–7 carbon atoms, e.g. cyclohexyl or an aryl group, e.g. an aromatic hydrocarbyl group of 6–18 carbon atoms, such as a phenyl, tolyl, or naphthyl, and Y is a chloride, bromide or preferably an iodide ion. Examples of the salts are tetrabutyl ammonium and phosphonium halides, benzyltriethyl ammonium and phosphonium halides, tetra octylammonium and tetraoctylphosphonium halides, and trioctyl and tributyl sulphonium halides. The salt as such may be mixed with the tin and zinc or may be obtained by reaction in situ of the halide reactant of formula RX with the corresponding tertiary amine or phosphine or sulphide or formula $R'_3N$, $R_3'P$ or $R'_2S$ preferably before addition of the tin and zinc. The groups R' in the quaternary or tertiary salt are preferably the same as R. The salt may be present in an amount of at least 0.1 g mole per g atom of tin, e.g. 0.1–1.5 g mole such as 0.1–0.8 and especially 0.4–0.8 g mole but is preferably present in an amount of at least 0.4, e.g. at least 0.6 molar proportion of salt per atomic proportion of tin, e.g. 0.6–1.5:1 especially 0.8–1.2:1, such as about 1:1. The mole amount of organotin product is often of the same order as the molar amount of the salt.

In addition to the salt the liquid contains tin and zinc which are preferably both solid, though if the temperature is high enough they are in the form of a molten alloy. The solid tin preferably has a maximum dimension of 5 mm, such as 50–1000$\mu$, especially 50–150$\mu$; it may be subdivided in the form of powder or comminuted material, or in sponge form or in the form of discs. The solid zinc is also preferably subdivided, e.g. with a maximum dimension of 5 mm, such as 50–1000$\mu$ especially 50–150$\mu$, e.g. in the form of powder or comminuted material; it may be in the form of granules. The atomic ratio of zinc to tin is usually 0.5:1 to 5:1, preferably 1:1 to 4:1, e.g. 1.5:1 to 3.0:1, and especially 1.5:1 to 2.5:1; stoichiometry of the reaction suggests a ratio of about 2:1. While the tin and zinc are usually separate in elemental form, they may be in the form of a solid or liquid alloy consisting essentially of tin and zinc, usually in the desired atomic ratio for use in the process. The suspension is usually agitated, e.g. by stirring.

If the melting point of the salt is below the reaction temperature, the molten salt can provide the necessary liquid phase for the reaction and is the sole organic liquid present, as is preferred. If desired an organic diluent may be present and should have a boiling point under the reaction pressure substantially higher than the reaction temperature, e.g. at least 50° C. higher and be inert to the reactants. Examples of such diluents are high boiling paraffin oils of b.p. greater than 300° C., dodecane, tetradecane or tetralin. The diluent is needed to provide a liquid phase if the salt has a melting point higher than that of the reaction temperature or if the proportion of salt to the combined weight of tin and zinc is insufficient to provide an agitatable suspension. The minimum proportion of salt depends on the form of the tin and zinc; less salt can be used satisfactorily with powdered tin or zinc than with tin discs or zinc granules. However, where possible the reaction is carried out in the absence of any inert organic liquid diluent. The weight proportion of liquid phase (i.e. salt and diluent (if present) but excluding organic halide and organotin product) to the combined total weight of zinc and tin is preferably 0.10:1 to 10:1, though higher proportions may be used; the proportion is more preferably 0.5:1 to 5:1, e.g. 1:1 to 4:1.

The organic halide is preferably added to the hot suspension over the course of the reaction; the halide may be dropped onto the surface of the suspension but is preferably passed in under its surface. The temperature and pressure conditions of the reaction may be such that unreacted organic halide (and especially substantially all of the unreacted halide) evaporates and forms a gaseous effluent. The rate of addition of organic halide is usually then not very much greater than the rate of reaction in order to optimize production of organotin while minimizing the amount of unreacted organic halide in the effluent. As alkyl halides tend to decompose at high temperature, the rate of addition of organic halide and the temperature and pressure are usually also such that the total of the rate of reaction and rate of evaporation of halide into the effluent is at least twice and preferably at least 10 times the rate of decomposition of the halide.

Thus the temperature, pressure and rate of addition of organic halide depend on at least six factors. The first is the essential need for at least some of the tetraorganotin product to be in the liquid phase, i.e. the liquid should be at a temperature below the boiling point of the tetraorganotin under the pressure pertaining over the liquid. Preferably the pressure and temperature are such that at least 50% and especially at least 90% of the tetraorganotin is in the liquid, the remainder (if any) being in a gaseous effluent. The second factor is the nature of the organic halide as it affects the rate of reaction, short chain alkyl halides reacting faster than long chain halides and iodides reacting faster than bromides, and chlorides. The third factor is the nature of the organic halide as it affects the rate of decomposition of the halides in the reaction medium for the order of stability of the alkyl halides is primary > secondary > tertiary. The fourth factor is the nature of the organic halide as it affects the stability of the tetraorganotin product in the reaction medium. The fifth factor is the nature of the salt because at too high a temperature the salts thermally decompose. The sixth factor is the need during the stepwise addition of halide for any unreacted organic halide (if unstable in the reaction medium at the temperature) to evaporate from the liquid forming a gaseous effluent so that if the reaction temperature is lower than the boiling point of the halide under atmospheric pressure, a reduced pressure is used under which the halide boils; a reduced pressure may be used in any event to enhance the rate of evaporation. It is not essential, however, that the unreacted organic halide evaporates if it is stable in the medium. Preferably, however, whether the unreacted halide evaporates or not, the halide is added at about the same rate as it reacts.

Alternatively, all the organic halide may be added in one portion from the start of the reaction, but this is less preferred as the reaction is exothermic.

Simple experiments can be carried out to determine suitable conditions of temperature, pressure and rate of addition applicable for any particular organic halide and salt. As a guide to temperature and pressure conditions, suitable conditions for butyl halides are reaction at 150°–250° C., e.g. 150°–190° C. under atmospheric pressure, and for octyl halides are reaction at 150°–300° C. preferably 150°–250° C., e.g. 150°–220° C. under 10–760 mm Hg pressure, e.g. 150°–190° C. such as 150°–170° C. under atmospheric pressure. Thus preferably, the reaction is carried out with butyl chloride by addition thereof over the course of the reaction to a liquid above the boiling point of butyl chloride so that unreacted chloride may evaporate, but the octyl chloride may be added in one portion or over the course of reaction to the liquid at below the boiling point of the halide.

The reaction time depends on the nature of the organic group and the halogen in the halide, the reaction temperature, the presence or absence of iodide ion in the reaction mixture, the proportion of 'onium catalyst and the degree to which the reaction is taken to completion. The reaction time is reduced with an increasing reactivity of the halide to nucleophilic attack, en increasing reaction temperature, the presence of iodide ion, an increasing amount of 'onium catalyst and a decreasing degree of reaction. However, reaction times of 1 to 24 hours at 150°–200° C. are often suitable.

In a particularly preferred aspect, the invention provides a process wherein an organic chloride which is butyl or octyl chloride, is passed into a suspension of solid zinc and solid tin in an atomic proportion of at least 0.5:1 in a molten salt of formula $R_4'N^+Y^-$ or $R_4'P^+Y^-$, wherein each $R'$ is butyl when butyl chloride is reacted or octyl when octyl chloride is reacted, and $Y^-$ is a chloride, bromide or iodide ion, at 130°–180° C., the molar ratio of organic chloride to salt being in the range 4:1 to 7:1 and the molar proportion of salt to tin being 0.6:1 to 1.5:1 to give tetrabutyltin or tetraoctyltin.

The reaction is usually carried out in an apparatus capable of condensing any gaseous effluent from the reaction. Any gaseous effluent from the reaction comprises unreacted organic halide but may also contain some tetraorgano tin compound. The unreacted halide in a continuous or repeated batch process can be recycled for reuse, optionally after removal of any tetraorganotin compound, e.g. by fractional distillation.

When the reaction has been taken to the desired degree of completion, the suspension contains the tetraorganotin compound, the salt, any unreacted tin and any unreacted zinc, and by product zinc chloride; it may or may not be substantially free of unreacted organic halide and may also contain a tri organotin halide. The liquid may be reused, once the organotin compound(s) has been removed and once the zinc chloride byproduct has also been separated.

The suspension may be worked up by allowing it to settle, when an upper liquid phase usually separates from a lower suspension phase which also contains unreacted tin and/or zinc. The upper phase comprises the organotin product and, if the reaction was carried out in the absence of a diluent usually consists substantially of the organotin product. The lower phase comprises the salt, any unreacted tin and/or zinc and by-product zinc chloride. Unreacted organic halide (if any) may be present in either phase, and may be separated from the organotin product by fractional distillation and may be separated from the lower phase or recycled for reuse. Preferably the reaction suspension is separated hot into a liquid organotin fraction and a lower liquid suspension, from which any tin and/or zinc residue can be filtered; the metal residue can be mixed with the necessary amount of fresh tin and/or zinc for reuse. Optionally the reaction suspension hot or cold or the lower phase hot or cold may be mixed with an organic solvent to aid the filtration stage. Examples of suitable solvents are ketones of 3–6 carbon atoms, e.g. acetone, methyl ethyl ketone and methyl isobutyl ketone, and alkanols of 1–6 carbon atoms, e.g. methanol, ethanol, propanols or butanols, and ethers, such as cyclic ones, e.g. dioxan and tetrahydrofuran or dialkyl ethers.

The mixture of 'onium salt and zinc chloride in the residual liquid, which has been separated from any unreacted tin and/or zinc, may itself be separated by being treated with aqueous alkali, e.g. an aqueous solution of an alkaline metal or alkaline earth metal hydroxide such as sodium or potassium hydroxide and the product extracted with an organic water immiscible solvent, such as a chlorinated aliphatic hydrocarbon, e.g. of 1–4 carbon atoms such as chloroform, 1,2-dichloroethane and methylene dichloride, to give an organic layer comprising the 'onium hydroxide and an aqueous phase containing the zinc; the phases are separated, and the 'onium halide salt made from the hydroxide by treatment with the appropriate hydrogen halide. The solubility of quaternary 'onium chlorides and hydroxides in organic media is described by Brändström et al Acta. Chem. Scand. 1969, 23, 1215 and subsequent papers.

The organic phase may consist substantially of the organotin product or may be a mixture of the organotin product and solvent and/or unreacted organic halide; in the latter case the solvent and/or organic halide are distilled from the organic phase leaving an organotin fraction. The organotin product may be purified by distillation if desired to remove small amounts of salts, solvent and any unreacted organic halide. The organotin compound usually comprises at least 50%, e.g. at least 70% and preferably at least 90% especially at least 95% such as 95–98%, of tetra organotin, the remainder being essentially triorganotin halide, in both of which the organic group is primarily based on the organic group in the organic halide but mixed products including organic groups from the salts may also be formed. Alternatively, in the case of the tetraorganotin compounds from alkyl halides of 2 to 4 carbon atoms, especially ethyl halides and to a lesser extent propyl halides, at the end of the reaction the temperature/pressure conditions can be altered to distil off the organotin compound but this operation is less desirable than that involving extraction, as higher temperatures encouraging decomposition and/or very low pressures are often needed. The tetra organotin product may be used for preparing triorganotin halo compounds, e.g. triorganotin chlorides substantially free from di and mono organotin compounds by mixing with the appropriate molar proportion of stannic halide, e.g. stannic chloride; similarly the corresponding diorgano and monoorganotin halides may be prepared.

The higher is the proportion of tetraorganotin to triorganotin halide in the organotin product, the higher is the volume efficiency of the plant producing the organotin product. The organotin halides are used as antifungal compounds or as intermediates for making such compounds or stabilizers, e.g. dibutyltin bis(isooctylthioglycollate), for polymeric materials, e.g. PVC. In particular the tetraalkyltin compounds may be disproportionated with stannic chloride to give a 2:1 molar mixture of mono alkyltin trihalide and dialkyltin dihalide useful as an intermediate for making mixtures of stabilizers, e.g. mercapto ester stabilizers for PVC.

The invention is illustrated in the following Examples:

EXAMPLE 1

Into a reaction flask fitted with a stirrer, a dropping funnel, thermometer and exit tube leading to a condenser and receiver, was placed tin powder (59.35 g, 0.5 g atom), zinc powder (65.35 g, 1.0 g atom), and tetra n-butyl ammonium iodide (73.8 g, 0.2 mole). The mixture was heated to 160°–180° C. to give a liquid suspension, which was stirred while n-butyl chloride (185 g, 2.0 mole) was slowly added with the temperature maintained at 160°–180° C. The rate of addition was about 46 g/hr. Unreacted butyl chloride evaporated and collected as condensate in the receiver. After 1 hr, specimens of the condensate and liquid were taken and analyzed for their organotin content; the condensate was free of organotin while the liquid contained tetrabutyltin without any tributyltin halide. The butyl chloride was added over 4 hr. The reaction mixture was allowed to cool and then acetone (about 75 ml) added to give an organic phase consisting substantially of organotins and liquid phase containing acetone, zinc, tin, zinc chloride and quaternary salt. The condensate (49.0 g) contained 2.7% of tetrabutyltin. The organic phase (57.5 g) contained 91.8% tetrabutyltin and 3.4% tributyltin chloride.

EXAMPLE 2

The process of Example 1 was repeated with n-octyl chloride (99 g, 0.67 mole), tin powder (29.67 g, 0.25 g atom), zinc powder (32.67 g, 0.5 g atom), tetra n-butyl ammonium iodide (73.8 g, 0.2 mole), a reaction temperature of 180°–200° C., and a time of addition of the octyl chloride of 5 hr. The organic phase produced after addition of acetone (about 75 ml) to the cooled reaction mixture weighed 42.0 g and contained by gas liquid chromatographic analysis a substantial proportion of tetraoctyl tin, but also mixed butyl octyltins and tri octyltin chloride. The condensate (octyl chloride) weighed 21.2 g.

EXAMPLE 3

Into a reaction flask fitted with a stirrer, a dropping funnel, thermometer and exit tube leading to a condenser and receiver, was placed tin powder (29.7 g, 0.25 g atom), zinc powder (32.7 g, 0.5 g atom), and tetra n-octyl phosphonium iodide (60.0 g, 0.1 mole). The mixture was heated to 170°–180° C. to give a liquid suspension, which was stirred while n-octyl chloride (90.5 g, 0.61 mole) was slowly added with the temperature maintained at 170°–180° C. The rate of addition was about 15 g/hr. After 6 hours, the above amount of octyl chloride had been added, at this time volatile compounds had started to collect in the receiver. The reaction was stopped. The reaction mixture was allowed to cool and then acetone added to give an organic phase consisting substantially of organotins and liquid phase containing acetone, zinc chloride, zinc, tin, and quaternary salt. The organic phase contained about 57 g organotins (about 0.095 mole tetra n-octyl tin and 0.005 mole other organotins).

EXAMPLE 4

The process of Example 3 was repeated with a reaction temperature of 165°–180° C., addition of octyl chloride over 1.25 hrs. in amount of 100 g (0.67 moles). The reaction liquid was analysed by Vapour Phase Chromatography (VPC) during and after the reaction and organotin product was predominantly tetra octyltin. The stirring was stopped and a top layer consisting essentially of organotins separated from a lower layer.

COMPARATIVE EXAMPLE A

The experiment of Example 4 was continued with addition of further octyl chloride (50 g) over 0.75 hours at 150°–170° C. Volatile compounds were given off during this period. Acetone extraction of the cooled reaction product gave an extract which VPC showed contained an increasing proportion of triorganotin chloride to tetraoctyltin over that of Example 4, namely 93% trioctyltin halide and 7% tetraoctyltin.

EXAMPLES 5–7

The process of Example 3 was repeated with the following molar amounts of octyl chloride, and tetra octyl phosphonium iodide salt, and g atoms of tin and zinc, and reactions at 155°–180° C.

| Example | Moles octyl chloride | g. atom of Sn | g. atom of Zn | Ratio Zn : Sn | Moles Salt | Mole ratio octyl chloride to salt |
|---|---|---|---|---|---|---|
| 5 | 1.68 | 0.25 | 0.5 | 2 : 1 | 0.25 | 6.7 : 1 |
| 6 | 0.67 | 0.125 | 0.5 | 4 : 1 | 0.1 | 6.7 : 1 |
| 7 | 0.67 | 0.25 | 0.5 | 2 : 1 | 0.1 | 6.7 : 1 |

In the cases of Examples 5 and 6, the octyl chloride was added uniformly over 2 hr., but in the case of Example 7, the octyl chloride was present from the start of the reaction, which was continued for 0.5 hr. In all three cases, addition of more octyl chloride gave volatile products believed to comprise octene, which from Comparative Example A corresponds to the production of tri octyltin chloride. VPC analysis on the reaction liquid during the reactions up to the addition of the extra octyl chloride shows the presence in the organotin product of substantially only tetraoctyltin, e.g. 95–98% tetraoctyltin and 2–5% trioctyltin chloride. At the end of the reactions, the stirring was stopped and the top organotin layer separated from the lower layer. The yield of organotin compound was 40% in Example 7 based on the tin added to the reaction.

EXAMPLE 8

The process of Example 3 was repeated with tin (0.125 g atom), zinc (0.25 g atom) and tetra octylphosphonium iodide (0.05 g mole) at 150°–170° C. with n-octyl iodide being added dropwise. The progress of the reaction was monitored by analysis by vapour phase chromatography. Up to the addition of about 132 g octyl iodide (0.55 g mole) which took about 2 hrs. the organotin product was about 95% tetraoctyltin and 5% trioctyltin iodide. When the total addition was about 144 g (0.6 mole) the organotin product was about 70% tetraoctyltin and 30% trioctyltin iodide with some vapour fraction, believed to be octene. The stirring was stopped, the reaction mixture was allowed to separate into 2 phases at above 100° C. The top layer consisted substantially of organotins and was separated from the lower phase containing the iodide salt, tin, zinc and zinc iodide as well as the excess of octyl iodide.

I claim:

1. A process for preparing organotin compounds containing at least 50% tetraorganotin and at most 50% triorganotin halide which comprises reacting an organic halide of formula RX where R is an alkyl group of 1 to 20 carbon atoms or alkenyl group of 2-20 carbon atoms and X is a chlorine, bromine or iodine atom, with a heated suspension of metallic material selected from the group consisting of (i) a mixture of zinc and tin, and (ii) an alloy consisting essentially of tin and zinc, the atomic proportion of zinc to tin in said material being at least 0.5:1, in a liquid comprising at least one 'onium salt, which is an organic quaternary ammonium or phosphonium salt or tertiary sulphonium salt, to produce a mixture containing tetraorganotin, and at least some of said tetraorganotin is in the liquid.

2. A process according to claim 1 wherein the organic halide is passed into the heated suspension over the course of the reaction.

3. A process according to claim 1 wherein the molar proportion of organic halide to 'onium salt is less than a critical proportion such that the tetra organotin compound produced contains less than 10% of triorganotin halide.

4. A process according to claim 1 wherein the suspension is heated to 130°-200° C.

5. A process according to claim 1 wherein the organic halide is an alkyl chloride.

6. A process according to claim 1 wherein the organic halide is an alkyl halide of 3-8 carbon atoms.

7. A process according to claim 6 wherein the organic halide is butyl chloride or octyl chloride.

8. A process according to claim 1 wherein the atomic proportion of zinc to tin is from 1:1 to 4:1.

9. A process according to claim 1 wherein the molar ratio of salt to tin is at least 0.4:1.

10. A process according to claim 9 wherein the molar ratio of salt to tin is 0.8:1 to 1.2:1.

11. A process according to claim 1 wherein the salt is of the formula $R'_4N^+Y^-$ or $R'_4P^+Y^-$, wherein each $R'$ is an alkyl group of 1 to 12 carbon atoms and Y is a chloride, bromide or iodide.

12. A process according to claim 11 wherein each $R'$ in the salt is the same as the R group in the organic halide.

13. A process according to claim 1 wherein there is an iodide present in the liquid during the reaction.

14. A process according to claim 1 wherein in the suspension the only organic liquid is molten quaternary ammonium or phosphonium salt.

15. A process according to claim 11 wherein an organic chloride which is butyl or octyl chloride, is passed into a suspension of solid zinc and solid tin in an atomic proportion of at least 0.5:1 in a molten salt of formula $R_4'N^+Y^-$ or $R_4'P^+Y^-$, wherein each $R'$ is butyl when butyl chloride is reacted or octyl when octyl chloride is reacted, and $Y^-$ is a chloride, bromide or iodide ion, at 130°-180° C., the molar ratio of organic chloride to salt being in the ratio of 4:1 to 7:1 to give tetrabutyltin or tetraoctyltin.

16. A process according to claim 1 wherein at the end of the reaction, said liquid containing said tetraorganotin is allowed to settle whereby it separates into an upper layer comprising tetraorganotin product and a lower layer, and the upper layer is separated.

17. A process according to claim 15 wherein the molar proportion of salt to tin is between 0.6:1 and 1.5:1.

18. A process for preparing organotin compounds containing at least 50% tetraorganotin and at most 50% triorganotin halide which comprises reacting an organic halide of formula RX where R is an alkyl group of 1 to 20 carbon atoms or alkenyl group of 2-20 carbon atoms and X is a chlorine, bromine or iodine atom, with a heated suspension of metallic material selected from the group consisting of (i) a mixture of zinc and tin, and (ii) an alloy consisting essentially of tin and zinc, the atomic proportion of zinc to tin in said material being at least 0.5:1, in a liquid at a temperature of 100°-300° C. comprising at least one 'onium salt, which is an organic quaternary ammonium or phosphonium halide or tertiary sulphonium halide, to produce a mixture containing tetraorganotin, and at least some of said tetraorganotin is in the liquid, said organic halide being in a molar proportion of said 'onium salt of up to 7:1.

19. A process according to claim 18 wherein the suspension is heated to 130°-200° C.

20. A process according to claim 18 wherein the molar ratio of salt to tin is at least 0.4:1.

21. A process according to claim 18 wherein the salt is of formula $R'_4N^+Y^-$ or $R'_4P^+Y^-$, wherein each $R'$ is an alkyl group of 1 to 12 carbon atoms and Y is a chloride, bromide or iodide.

22. A process according to claim 18 wherein there is an iodide present in the liquid during the reaction.

23. A process according to claim 18 wherein in the suspension the only organic liquid is molten quaternary ammonium or phosphonium halide.

24. A process according to claim 18 wherein at the end of the reaction, said liquid containing said tetraorganotin is allowed to settle whereby it separates into an upper layer comprising tetraorganotin product and a lower layer, and the upper layer is separated.

* * * * *